United States Patent [19]

Fuganti et al.

[11] Patent Number: 5,079,146
[45] Date of Patent: Jan. 7, 1992

[54] METHOD OF PROTECTION OF THE CARBOXY GROUPS IN THE CHEMISTRY OF β-LACTAM COMPOUNDS

[75] Inventors: Claudio Fuganti; Eva Baldaro, both of Milan; Daniela Faiardi, Pavia; Ameriga Lazzarini, Uboldo, all of Italy

[73] Assignee: Sclavo S.p.A., Siena, Italy

[21] Appl. No.: 333,091

[22] Filed: Apr. 4, 1989

[30] Foreign Application Priority Data

Apr. 8, 1988 [IT] Italy ............................. 20131 A/88

[51] Int. Cl.$^5$ ..................... C12P 37/00; C12P 35/00
[52] U.S. Cl. ................................. 435/47; 435/43; 435/44; 435/45; 435/46; 435/48; 435/49; 435/50; 435/51; 435/230
[58] Field of Search ................ 435/45, 44, 43, 46, 435/47, 48, 49, 50, 51, 136, 230

[56] References Cited

U.S. PATENT DOCUMENTS

| | | | |
|---|---|---|---|
| 3,239,427 | 3/1966 | Huang et al. | 435/44 |
| 3,284,451 | 11/1966 | Cheney et al. | 435/47 |
| 3,528,965 | 9/1970 | Cole et al. | 435/43 |
| 3,880,713 | 4/1975 | Fleming et al. | 435/44 |
| 3,945,888 | 3/1976 | Takahashi et al. | 435/50 |
| 3,972,774 | 8/1974 | Brannon et al. | 435/47 |
| 4,413,056 | 11/1983 | Chester et al. | 435/43 |

FOREIGN PATENT DOCUMENTS

| | | | |
|---|---|---|---|
| 218323 | 4/1987 | European Pat. Off. | 435/43 |
| 283218 | 9/1988 | European Pat. Off. | 435/50 |
| 2086897 | 5/1982 | United Kingdom | 435/43 |
| 2206578 | 1/1989 | United Kingdom | 435/43 |

*Primary Examiner*—Carolyn Elmore
*Attorney, Agent, or Firm*—Oblon, Spivak, McClelland, Maier & Neustadt

[57] ABSTRACT

The present invention relates to a new method of protection of the carboxy group in the chemistry of the compounds of β-lactam type. According to such a method, the carboxy group is protected by being transformed into its corresponding phenyl-acetoxy-methyl ester, which is then removed by an enzymatic route by means of penicillinacylase.

In particular, if the β-lactam compound also bears a phenyl-acetamidic substitutent, this latter is simultaneously hydrolysed during the same step of removal of the carboxy function protecting group.

3 Claims, No Drawings

METHOD OF PROTECTION OF THE CARBOXY GROUPS IN THE CHEMISTRY OF β-LACTAM COMPOUNDS

The present invention relates to a new method of protection of the carboxy group in the chemistry of the β-lactam compounds. According to such a method, the carboxy group is protected by being converted into its corresponding phenyl-acetoxy-methyl ester. The removal of the protection is obtained by enzymatic way, by means of penicillinacylase (EC 3.5.1.11).

The problem of the protection of a carboxy group is a subject interesting a large number of chemical processes, and is largely felt in a so complex field as the chemistry of the β-lactam antibiotics is, in which many are the processes of modification and interconversion which have been developed by starting from particular structures belonging to this family of compounds, which are easily available from natural sources.

For example, the process of expansion of the thiazolidinic cycle of the penicillins to yield the typical backbone of cephalosporanic compounds is very important; and many other transformations are carried out on both penicillins and cephalosporins or penems in order to introduce substituents not otherways obtainable by natural way, in order to find out compounds endowed with a wider and more various spectrum of activity.

During such transformations, the protection is required often of the carboxy group which, if left as such, undergoes a decarboxylation [Morin JACS 91:1401 1969] or anyway leads to the formation of undesired byproducts [Gutowski Tetrahedron Letters 37:3433 (1971)].

In order to prevent such undesired reactions from taking place, several protecting groups have been found out which must be additionally endowed with the characteristic of being removable under such conditions as not to interfere with the sensitivity of the β-lactam ring. For example, this characteristic is found in the benzyl group and in the benzhydryl group, which are removed by hydrogenolysis; in p-methoxy-benzyl, which is hydrolysable with trifluoroacetic acid; in the p-nitrobenzyl group and in the β-trichloroethyl group, which ar removable with Zn and acetic acid [Woodword JACS 88:852 (1966)]; in pivalyl-oxy-methyl, which hydrolyses under mildly basic conditions; and in trimethyl-silyl, unstable in the presence of methyl alcohol or water [from Koning JOC 40:1346 (1975)].

Unfortunately, some of these protecting groups are removed with rather low removal yields, such as, e.g., benzhydryl, which undergoes hydrogenolysis with yields lower than 30% [Morin JACS 91:1401 1969)], or trichloroethyl, during the removal of which zinc ions are generated, which form complexes with some substrates of cephalosporanic type, rendering complex their separation from the reaction mixture, and which therefore have to be removed by using ion-exchange resins [Chauvette JOC 36:1259 (1971)]. On the contrary, other protecting groups, such as p-methoxy-benzyl have an influence on the yields of the process of expansion of the thiazolidinic ring [Chauvette JOC 36:1259 (1971)], or, such as trimethyl-silyl, liberate volatile products, which can cause pollution problems.

The present Applicant has found now that the carboxy functions of penicillins, cephalosphorins and, in general, of compounds of β-lactam type can be protected by being converted into their corresponding phenyl-acetoxy-methyl esters of structure:

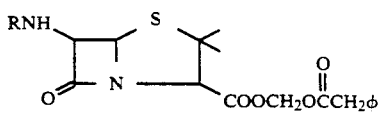

(I)

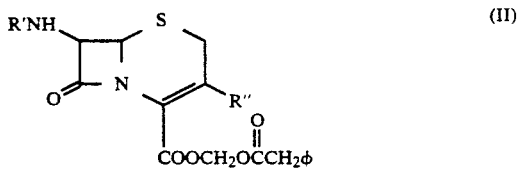

(II)

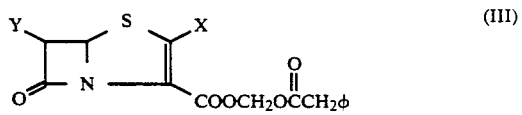

(III)

wherein R′=Me, OMe, Cl.

The removal of the protection is obtained by enzymatic way with penicillinacylase (E.C. 3.5.1.11).

In this way, the reaction can be carried out at room temperature, simultaneously avoiding both the use of expensive chemical reactants, and the formation of byproducts which are capable of generating environmental problems. The introduction of this protecting group results to be easily accomplished: it can be attained by means of the condensation of a molecule of the acid with a compound of formula

XCH₂OCOCH₂φ wherein preferred meanings for X are Cl, Br, I, CH₃SO₃—, CF₃SO₃, CH₃C₆H₄SO₃—, which latter in its turn is prepared from the chloride or bromide of phenylacetic acid, formaldehyde and zinc chloride [Bodor J. Med. 23:566 (1980)].

Also the removal of the protecting group is easily obtained by means of the enzyme in solution, or immobilized on a support, or in a membrane reactor. The use of the enzymatic system immobilized, e.g., on beads of polyamidic resin (Eupergit(R)C) enables it to be used for a considerably large number of cycles: in fact, a same enzyme batch, used for more than 400 cycles of hydrolysis did not show any meaningful loss of activity. The reaction conditions are clearly mild and require that the process be carried out at a temperature comprised within the range of from 0° to 55° C. and at a pH comprised within the range of from 5 to 9.5

Furthermore, by using this novel protecting group for such structures as (I), (II) and (III) in which R and R′ are φCH₂CO—, when the protection of the carboxy group is removed, the hydrolysis of the amidic substituent is simultaneously achieved during the same step.

This particular advantage can be exploited in such processes as those disclosed in the following, which therefore result to be accomplished with one step less than as known heretofore:

1)

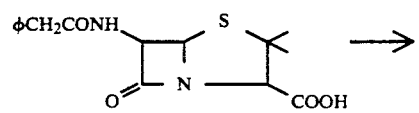

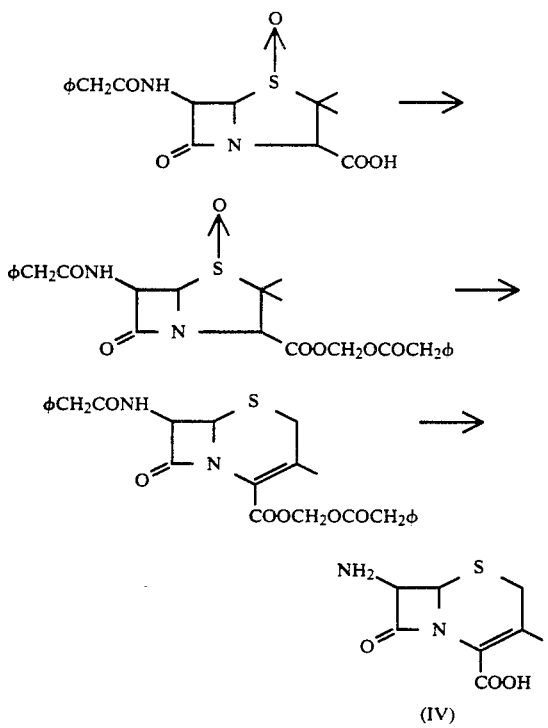

From 7-amino-deacetoxy-cephalosporanic acid (IV), all of the products of general formula:

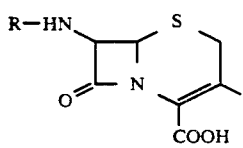

can be obtained.

2)

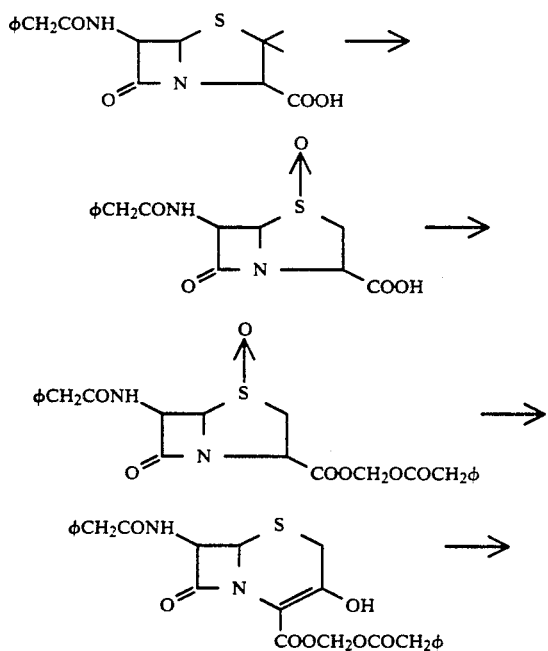

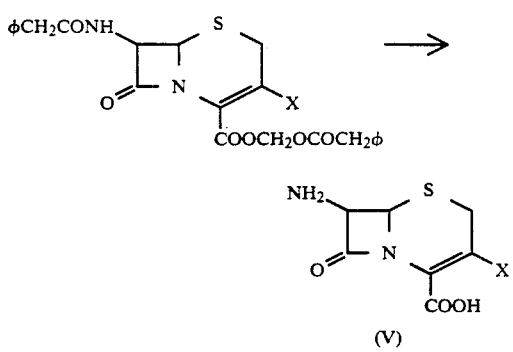

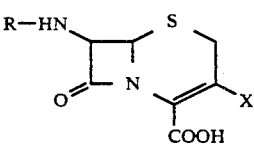

(V)

wherein X=OMe, Cl.

From 7-amino-3-methoxy-ceph-3-em-4-carboxy acid and 7-amino-3-chloro-ceph-3-em-4-carboxy acid (V), the compounds of general formula can be obtained.

From the HPLC analysis of the reaction mixtures of these processes, the present Applicant found that the hydrolysis of the ester group and of the amidic groups proceed at the same rate, and at any times one single reaction product is found, in the molar ratio of 1:2 to the phenylacetic acid.

No reaction intermediates were identified.

Therefore, a novel protecting groups for acids was found, which shows two major advantages: the first one is concerned with the easiness and the high yields with which it is removed without interfering with the reactivity of the β-lactam ring, and without using dangerous reactants; and the second one is concerned with the possibility of causing in such special substrates as some penicillins and cephalosporins which contain the phenyl-acetamidic substituent respectively in the 6- or in the 7-position, the simultaneous hydrolysis of this latter function too.

EXAMPLE

1) Benzylpenicillin sulfoxide

To 75 g (0.19 mol) of potassium salt of benzylpenicillin in 1 liter of water 45.5 g (0.20 mol) of sodium metaperiodate was added and the mixture was stirred for 2 hours at room temperature. After cooling to 0° C., the reaction mixture was extracted with chloroform at pH=1.

The organic phase was concentrated to a volume of 150 ml and 400 ml of ether was added to it, so as to cause benzylpenicillin sulfoxide to precipitate. Precipitated benzylpenicillin sulfoxide was filtered off, was washed with ether and was dried under reduced pressure. 64 g of product was obtained (90%).

2) Phenacetyloxymethyl ester of benzylpenicillin sulfoxide

To 50 g (0.16 mol) of benzylpenicillin sulfoxide dissolved in 140 ml of anhydrous DMF, 44 ml of triethylamine (0.32 mol) is added, and 58 g (0.32 mol) of phenacetyloxymethylene chloride is added dropwise at room temperature under a nitrogen blanketing atmosphere.

After 24 hours at room temperature, the reaction mass is poured into water and is extracted with methylene chloride.

The organic phase is then washed with very diluted acid and then with sodium bicarbonate and finally with water. The washed organic phase is thoroughly dried, is concentrated and the product is isolated by chromatography (eluent: hexane/AcOt 6:4, 2:8). 30 g of product is obtained, with a yield of 40%.

$[\alpha]_D^{20} = +167.98°$ (c=1 in CHCl$_3$)

3) Phenylacetoxymethyl ester of 7-phenylacetamido-deacetoxy-cephalosporanic acid A mixture of 10 g (0.02 mol) of phenacetyloxymethyl ester of benzyl-penicillin sulfoxide with 2.5 g of anydrous p-toluene-sulfonic acid in 250 ml of tetramethylurea is heated at 135° C. for 2 hours. The solvent is removed and the obtained oil is dissolved in 100 ml of ethyl acetate. The organic phase is washed with a diluted solution of sodium bicarbonate and is subsequently washed twice with water, is thoroughly dried and is evaporated. 8.6 g of solid product is obtained and is crystallized from ethyl acetate/hexane. Yield 90%. $[\alpha]_D^{20} = +71.89°$ melting point=150°-151° C.

4) 7-Amino-deacetoxy-cephalosporanic acid

200 I.U. of penicillinacylase supported on Eupergit (190 I.U./gram) is suspended in 300 ml of a 90:10 water-/acetonitrile mixture. To this system at 25° C., 400 mg of phenacetyloxymethyl ester of 7-phenylacetamidodeacetoxy-cephalosporanic acid dissolved in acetonitrile is added dropwise, with the pH value of the solution being maintained within the range of from 7.3 to 7.5 by means of the addition of 0.1N NaOH. When the theoretical amount of NaOH results to be consumed (2 equivalents per mol), the enzyme is filtered off, the filtrate is acidified to pH 5 by means of the addition of HCl, and phenylacetic acid is extracted with ethyl acetate. The volume of the aqueous phase is reduced by vacuum concentration, with 178 mg of product being obtained.

We claim:

1. A process for converting a β-lactam compound of the formula

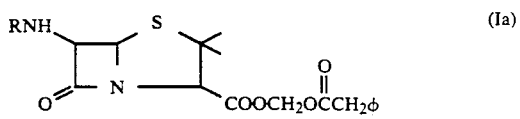

or

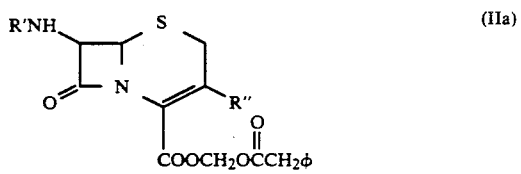

wherein R and R' are each φCH$_2$C(O)—, R" is a methyl group, a methoxy group or a chlorine atom and φ is a phenyl group, into a compound of the formula

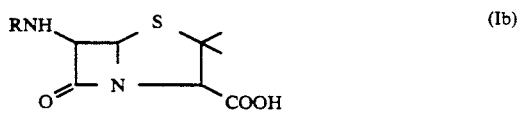

or

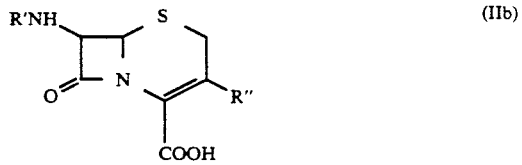

respectively comprising contacting said compound of the formula (Ia) or (IIa) with penicillinacylase (E.C. 3.5.1.11) at a temperature within the range of from 0° to 55° C., at a pH within the range of from 5 to 9.5.

2. The process according to claim 1, wherein said compound of the formula (IIa), wherein R" is methyl group, is prepared by: oxidizing the potassium salt of benzylpenicillin to form benzylpenicillin sulfoxide, contacting said benzylpenicillin sulfoxide with phenacetyloxymethylene chloride to form the phenacetyloxymethyl ester of benzylpenicillin sulfoxide, and then expanding the ring of said phenacetyloxymethyl ester of benzylpenicillin sulfoxide to form the phenacetyloxymethyl ester of 7-phenylacetamido-deacetoxy-cephalosporanic acid of formula (IIa).

3. The process according to claim 1, wherein said enzyme is immobilized on a support.

* * * * *